(12) United States Patent
Saliger

(10) Patent No.: US 7,367,801 B2
(45) Date of Patent: May 6, 2008

(54) METHOD FOR PRECISELY-POSITIONED PRODUCTION OF A CAVITY, ESPECIALLY A BONE CAVITY AND INSTRUMENT THEREFOR

(75) Inventor: Günter Saliger, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 10/531,986

(22) PCT Filed: Oct. 27, 2003

(86) PCT No.: PCT/DE03/03571

§ 371 (c)(1),
(2), (4) Date: Apr. 20, 2005

(87) PCT Pub. No.: WO2004/039278

PCT Pub. Date: May 13, 2004

(65) Prior Publication Data

US 2006/0057534 A1    Mar. 16, 2006

(30) Foreign Application Priority Data

Oct. 25, 2002  (DE) ................................ 102 50 006

(51) Int. Cl.
*A61C 1/00* (2006.01)
*A61C 3/00* (2006.01)

(52) U.S. Cl. ........................................ 433/29; 433/75

(58) Field of Classification Search ................. 433/29, 433/75–76; 600/589–590
See application file for complete search history.

(56) References Cited

U.S. PATENT DOCUMENTS

| | | | |
|---|---|---|---|
| 4,837,732 A * | 6/1989 | Brandestini et al. .......... | 433/29 |
| 5,049,070 A * | 9/1991 | Ademovic .................... | 433/29 |
| 5,290,168 A * | 3/1994 | Cooper et al. ................ | 433/29 |
| 5,429,502 A   | 7/1995 | Cooper et al. | |
| 5,711,665 A * | 1/1998 | Adam et al. .................... | 433/9 |
| 6,334,772 B1* | 1/2002 | Taub et al. .................... | 433/24 |
| 6,419,484 B1* | 7/2002 | DaSilva et al. ............... | 433/29 |
| 2002/0072028 A1* | 6/2002 | Taub et al. .................... | 433/24 |

FOREIGN PATENT DOCUMENTS

| | | |
|---|---|---|
| DE | 40 09 438 A1 | 9/1991 |
| EP | 0 868 886 A1 | 10/1998 |

\* cited by examiner

*Primary Examiner*—John J. Wilson
*Assistant Examiner*—Hejdi M Bashaw
(74) *Attorney, Agent, or Firm*—Dykema Gossett PLLC

(57) ABSTRACT

The invention relates to a method for precisely-positioned production of a cavity, especially a bone cavity, at a preparation point by means of a hand instrument, comprising the following steps: calculation of position-dependent surface characteristics from a three-dimensional data set of the surface of the preparation point at a desired position of an implant which is to be inserted in said cavity, wherein the area in which the cavity is to be created is represented in the form of a three-dimensional data set of volume data; detection of at least one partial cut-out of the preparation point comprising an actual visible surface feature by means of a camera which is arranged on the hand instrument at a pre-defined distance to a processing tool and display as a video image; insertion of a calculated surface characteristic for the desired position of the hand instrument, wherein the inserted surface characteristic can be altered, especially made congruent with respect to its position in relation to the actual visible surface characteristic by modifying the position and the inclination of the hand instrument.

3 Claims, 7 Drawing Sheets

METHOD FOR PRECISELY-POSITIONED PRODUCTION OF A CAVITY, ESPECIALLY A BONE CAVITY AND INSTRUMENT THEREFOR

BACKGROUND OF THE INVENTION

The invention relates to a method of creating a cavity, in particular a bone cavity, in correct position, and to an instrument for carrying out said method.

Dental implantology involves the incorporation of exogenous fittings, or so-called implants, into the bone, in order to provide a substance-protecting prosthetic replacement of missing teeth and to provide edentate jaws with a fixed dental restoration.

In order to achieve long-lasting, successful treatment, various dental and anatomical constraints must be observed when such fittings are implanted. The transference of masticatory forces to the jaw-bone must be accomplished in such a way that the approved rules of biomechanics and dental prosthetics are observed. Body cavities may not be opened and nerve tracts may not be damaged. Finally, it is necessary to ascertain whether a quantitatively and qualitatively adequate supply of bony substance is present.

These constraints require making a thorough diagnosis prior to the intervention and planning a suitable strategy for carrying out the intervention. The ultimate goal is to achieve a good implementation of the strategy during the operation.

PRIOR ART

As a rule, the implantologist can use the currently available technology aids such as computer-assisted tomography (CAT), orthopantomography (OPG), and measurements of bone density and bone thickness to make an adequate diagnosis and use it to devise a good implantation strategy.

There are, however, major shortcomings as regards putting this strategy into practice.

In recent years attempts have been made to bridge this gap. Neurosurgical and orthopedic procedures have been used in doing so. Markings have been placed on the patient and the operating instruments for observance with the aid of twin cameras. The relative position of, say, a drill can be determined from the known geometry of the operating instruments and the markings. Using this principle it is possible to implement the implantion strategy effectively. With such procedures, it has been possible to achieve precision levels of 1 mm, or in other words, deviations as great as 1 mm might occur between the planned and the attained position.

The disadvantage of such equipment is its comparatively high price. Such equipment is thus only economically feasible for the insertion of a large number of implants.

It is thus an object of the invention to provide a more cost-effective solution to the problem described above, in order to make the insertion of only a few implants economically feasible.

DESCRIPTION OF THE INVENTION

The invention described herein is based on the idea that suitable surface features, such as the horizon line of a topographic surface can, in encoded form, also provide information on the position of the observer.

On this basis, a method of creating a cavity in a desired position at a preparation site is proposed, wherein, using a hand instrument, position-dependent surface features are computed from a three dimensional data set referring to the surface of the preparation site to give a target position for insertion of an implant into a cavity, the area in which the cavity is to be created and the implant subsequently inserted being displayed as a three dimensional spatial data set.

A camera mounted on a hand instrument at a specified distance from a machining tool records and displays, as a video image, a section of the preparation site showing at least one actually visible position-dependent surface feature. The computed position-dependent surface feature for the target position of the hand instrument will be superimposed on the video image, and by changing the position and angle of the hand instrument, the position of the superimposed position-dependent surface feature can be changed relatively to the actually visible position-dependent surface feature and, in particular, be brought into coincidence therewith.

By the term "camera" we mean all measuring equipment, imaging equipment, or image digitizing equipment capable of recording a section of the preparation site such that it can be displayed as a video image.

In this way it is possible to show the user whether his hand instrument is oriented correctly to create the cavity as planned, so that the implant can be inserted correctly at the target site.

The relative position of the X-ray image and the 3D data set is known from special markings, so-called X-ray-opaque markers, which are visible in both the spatial data of the X-ray image and in the 3D data set relating to the surface. The insertion site for the implant is determined by the implantologist with the aid of the X-ray image. In this manner the position of the insertion site relative to the 3D data set will also be known, and from this position the 3D data set is used to compute the position-dependent surface feature which would result when the drill is placed in the planned position and is angled to coincide with the planned drill axis.

Any suitable, visually displayable feature of a tooth or the preparation area that can be computed from the surface data and that enables a definition of a position may be used as a surface feature, a particularly suitable feature being a horizon line.

During machining, the computed position-dependent surface feature for the respective position of the hand instrument is always advantageously superimposed on the video image, wherein the position of the hand-held instrument corresponds to a position of the implant inside the cavity. This ensures that adjustments will still be possible even though the hand instrument would have been initially positioned correctly.

Advantageously, monitoring should be possible when the end position is reached, by showing a position-dependent surface feature for an end position of the machining tool in the cavity to be created.

The invention also relates to a hand instrument for creating or machining cavities, in particular bone cavities, which includes a machining tool. The hand instrument is equipped with a camera mounted at a known distance from the tip of the machining tool.

With such a hand instrument it is possible to scan the preparation site and compare it with a three dimensional data set of spatial data or surface data.

The camera advantageously has a depth of focus of from 5 to 30 mm and scans a panorama view. This permits orientation to the side showing the most pronounced orienting features of the 3D data set.

According to an additional embodiment, the video camera is built into that end of the instrument which is near to the machining tool. This permits exact registration of the actual horizon line of the reference image at the preparation site.

Finally, light sources can be provided to illuminate that part of the surface which is relevant for registering and displaying the horizon line, or to illuminate other distinctive features of the surface.

Furthermore, the hand instrument can be linked to a display for the image recorded by the camera, which display may also show data, provided by an evaluating unit, in the form of a horizon line or some other distinctive surface features.

BRIEF DESCRIPTION OF THE DRAWINGS

The method of the invention is illustrated below with reference to the drawings, in which.

Figure 1:
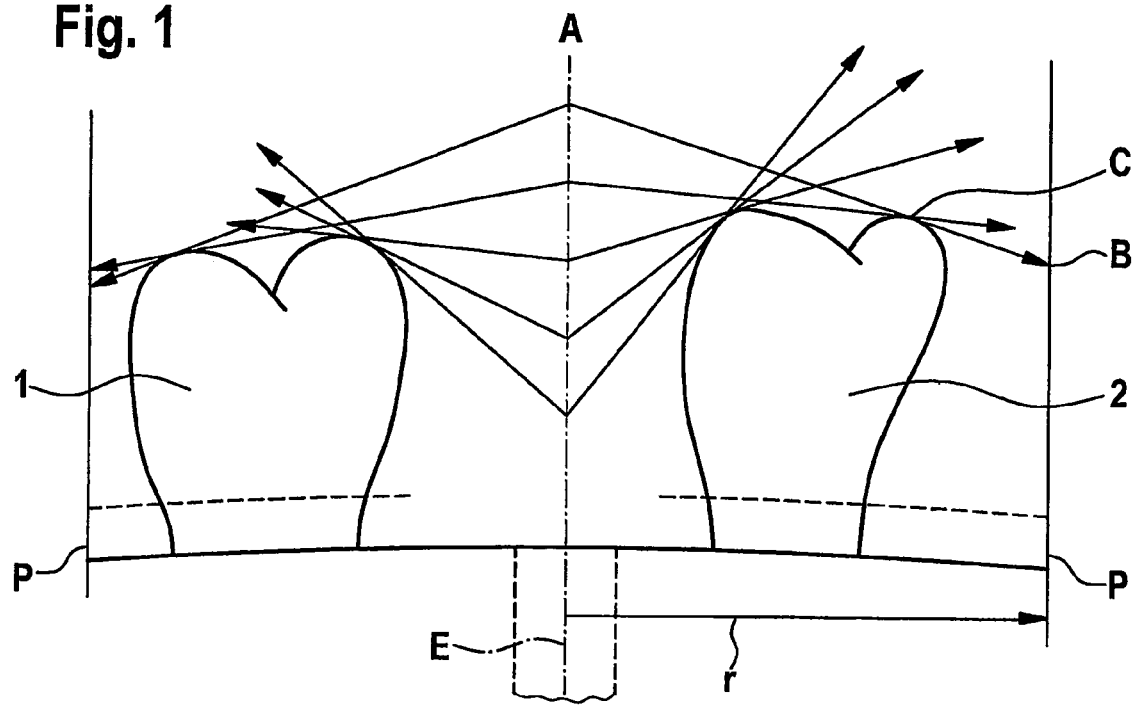
FIG. 1 shows a horizon line in a first view.
Figure 2:
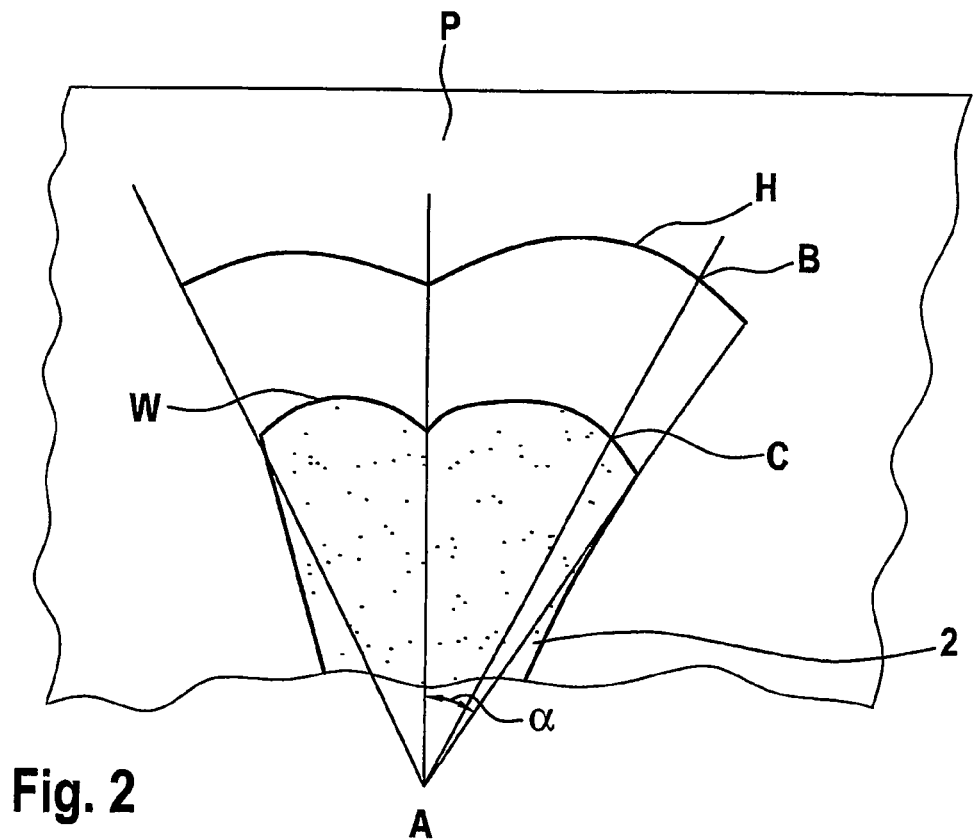
FIG. 2 shows a horizon line in a second view.

The concept of the horizon line as an example of a position-dependent surface feature is explained with the aid of FIGS. 1 and 2. A horizon line is characterized by the following imaging rule. An observer at point A constructs, say, a circular projection screen P around himself, which is covered with a transparent film and has a known radius r. Point B for each angle element alpha of the entire panorama is marked on screen P, and horizon C appears to lie on point B for the observer located at center point A. The image thus generated is designated as horizon line H. The distinguishing feature of horizon line H is that the location of the observer is also implicitly coded in its shape. Conversely, when an adequately defined, unique horizon line is known, it is possible to relocate the place from which said horizon line was observed.

It depends on the displayed objects themselves whether there is a clear correlation between the horizon line and the displayed objects. The more complex the objects are, the clearer the correlation will be. The following example illustrates this situation. From the photograph of a mountain range, one can determine the location from which this photograph was taken, if one also knows the route that was taken along the mountain range.

The spatial relationship between the measurement data recorded by surface scanning and the X-ray-generated spatial data is made known by the use of X-ray-opaque markers. The implant insertion site is determined with the aid of an X-ray image (OPG, CAT). The surface data coordinates thus obtained are used to monitor correct positioning of the tool while creating the cavity.

In doing so, the horizon lines of adjacent teeth 1, 2 or other suitable position-dependent surface features are taken into account.

The expected horizon lines along the direction of implant insertion are computed with the aid of the 3D data set. Thus, all points A lie on an axis E parallel to, but in particular coincident with, the insertion axis.

Figure 3:
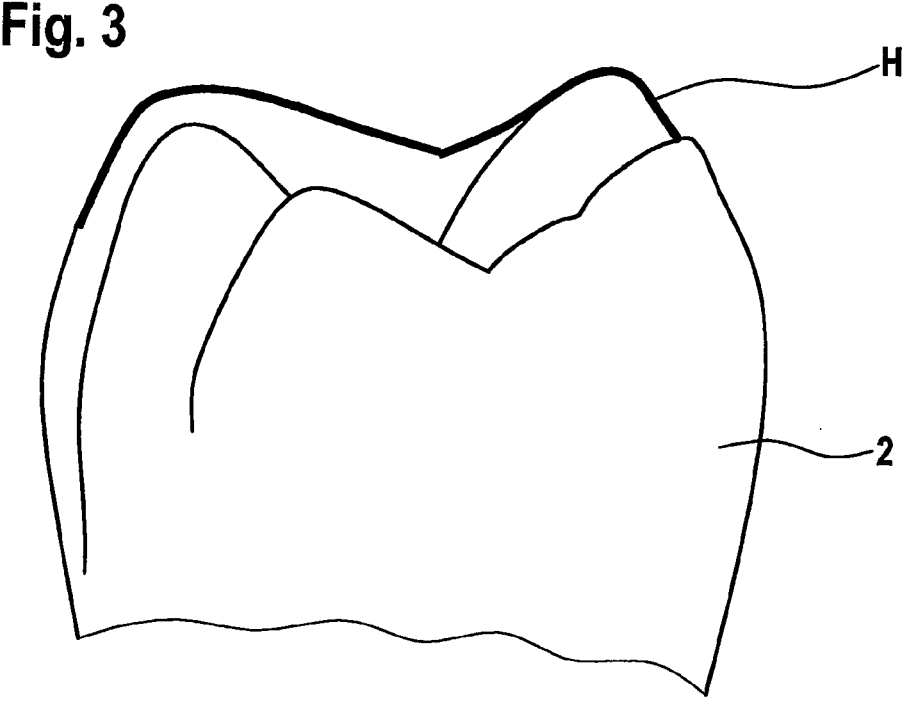
FIG. 3 shows a tooth and a target horizon line coinciding therewith.

FIG. 3 shows a diagram of a tooth 1, as it appears on a display when recorded through the optics of the machining tool. The thick line designates the horizon line H, which would be visible at the desired position of implant axis as defined in the strategy. In this case the true horizon and the horizon line are coincident. The present position of the drill is thus correct.

Figure 4:
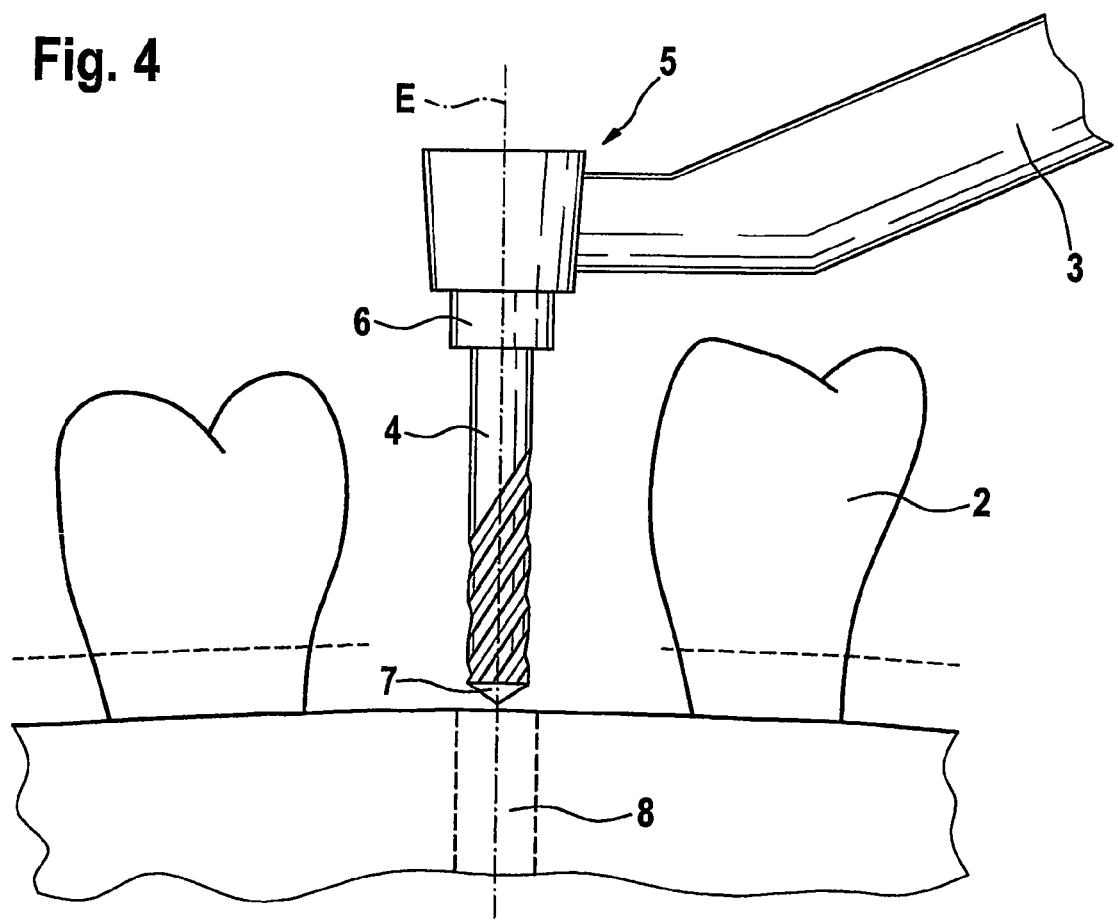
FIG. 4 illustrates correct positioning of the machining tool of the hand instrument.

FIG. 4 shows a machining instrument 3 having a tool 4, which is located at the predetermined position. At its end 5 near machining tool 4, hand instrument 3 possesses optical means accommodated in a small cylindrical attachment 6 and designed to record the surrounding area, for example a built-in intra-oral video camera. The distance between the tip 7 of the tool and the position of said optical means is known. Attachment 6 is located above tool 4 and accommodates the optical means and also an optical fiber bundle to illuminate the teeth.

Figure 6:
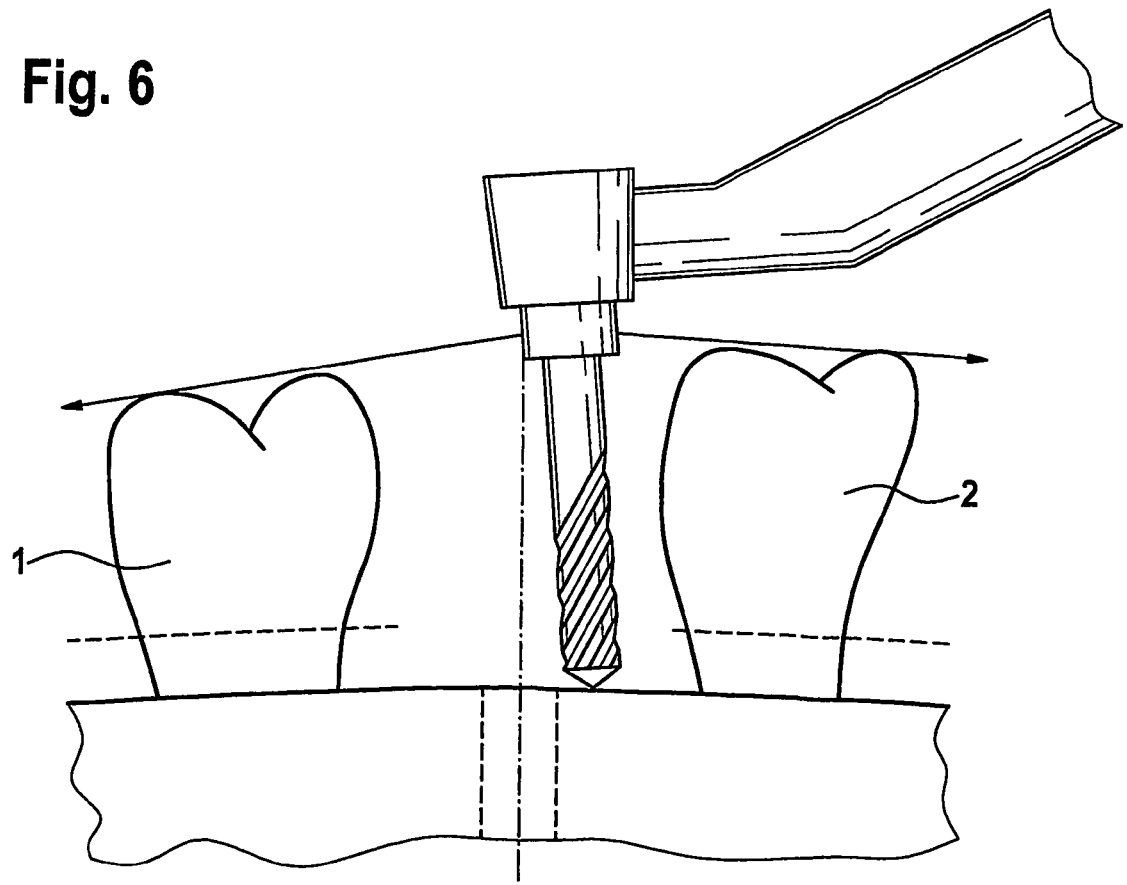
FIG. 6 illustrates incorrect positioning of the machining tool of the hand instrument.

The optics should have a field depth ranging from 5 to 30 mm. It must not be telecentric, that is, objects at different distances must be displayed as different in size. It may comprise 360 degree panorama optics, as indicated in FIG. 6. It is sufficient, however, to use an image field large enough to display one tooth. Thus the camera will then register tooth 1, 2 only from one direction.

In this way the adjacent teeth 1 and 2 are displayed in the model point of the implant drill hole 8 to be formed. It is important for the present procedure that the protuberances of the teeth stand out well, in a manner similar to the crests of mountains. Other distinct surface features may be provided, for example, by fillings. Here too, essentially all visible, position-dependent surface features are registered.

No special requirements apply as regards the optical distortion of the system. Essentially, a monochrome image is sufficient.

Figure 5:
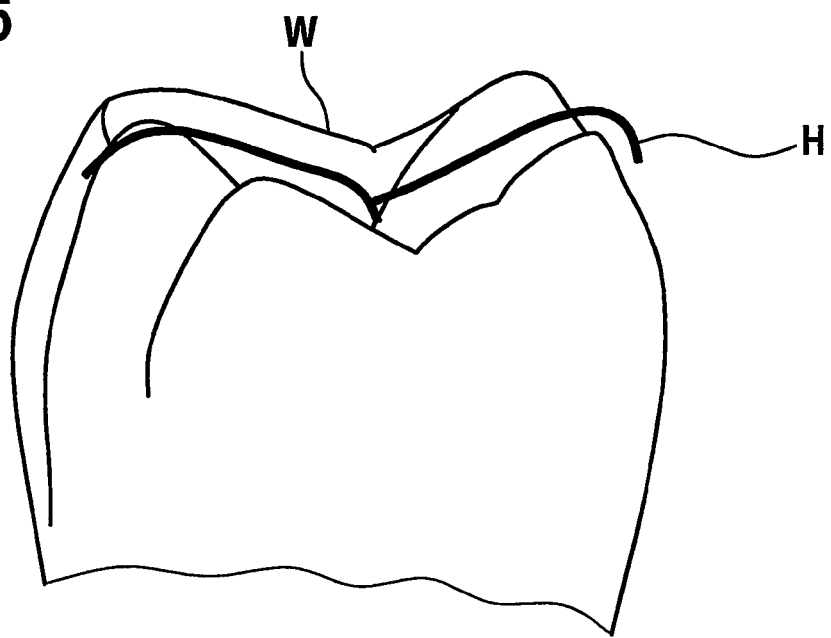
FIG. 5 shows a tooth and a non-coincident target horizon line.

FIG. 5 shows a diagram of a display, in which the true horizon W and the horizon line H are not coincident. The present position of the drill is not correct, see FIG. 6. The drill is not yet in the predetermined position.

Figure 7:
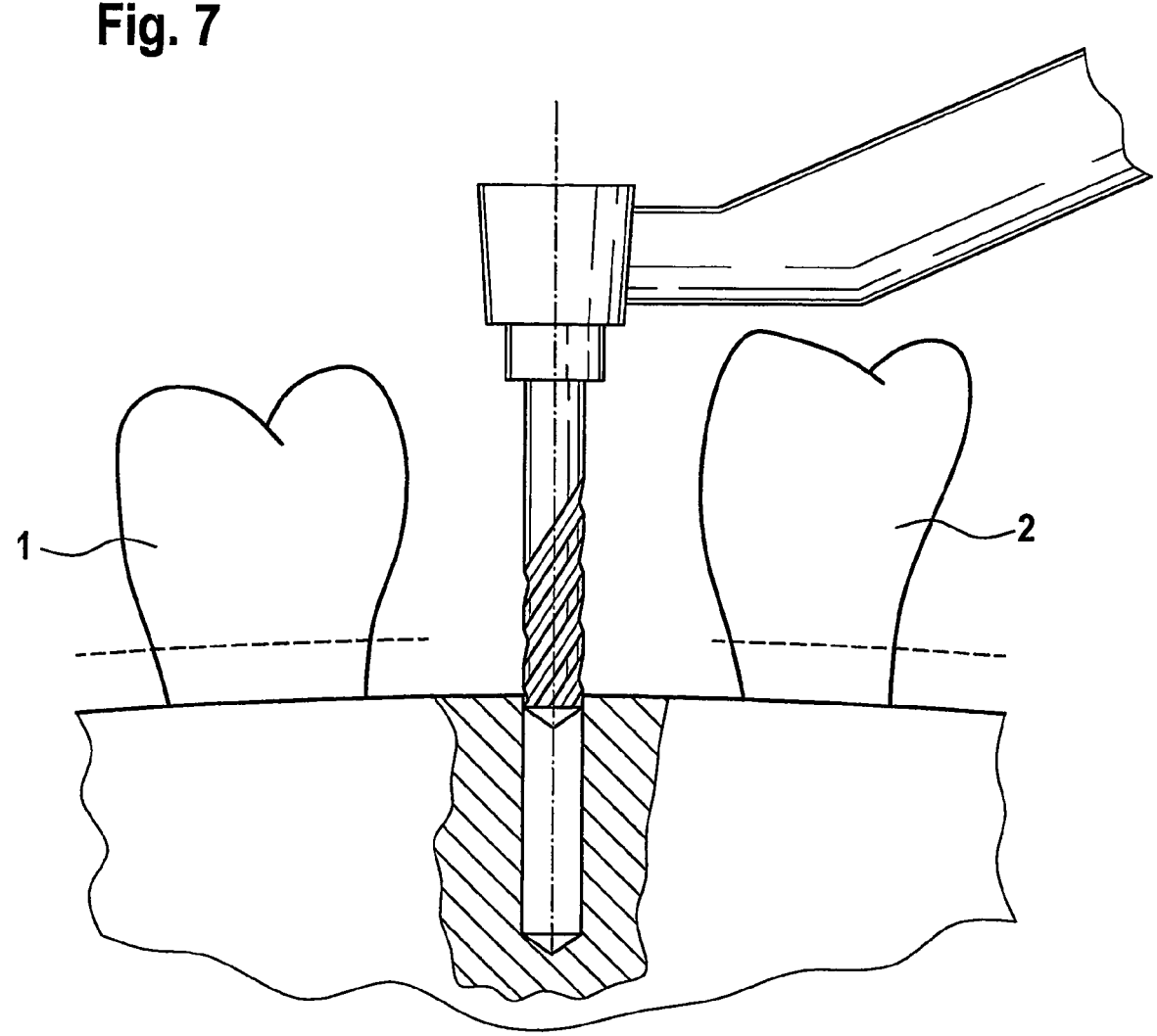
FIG. 7 illustrates correct positioning of the machining tool of the hand instrument during machining.
Figure 8:
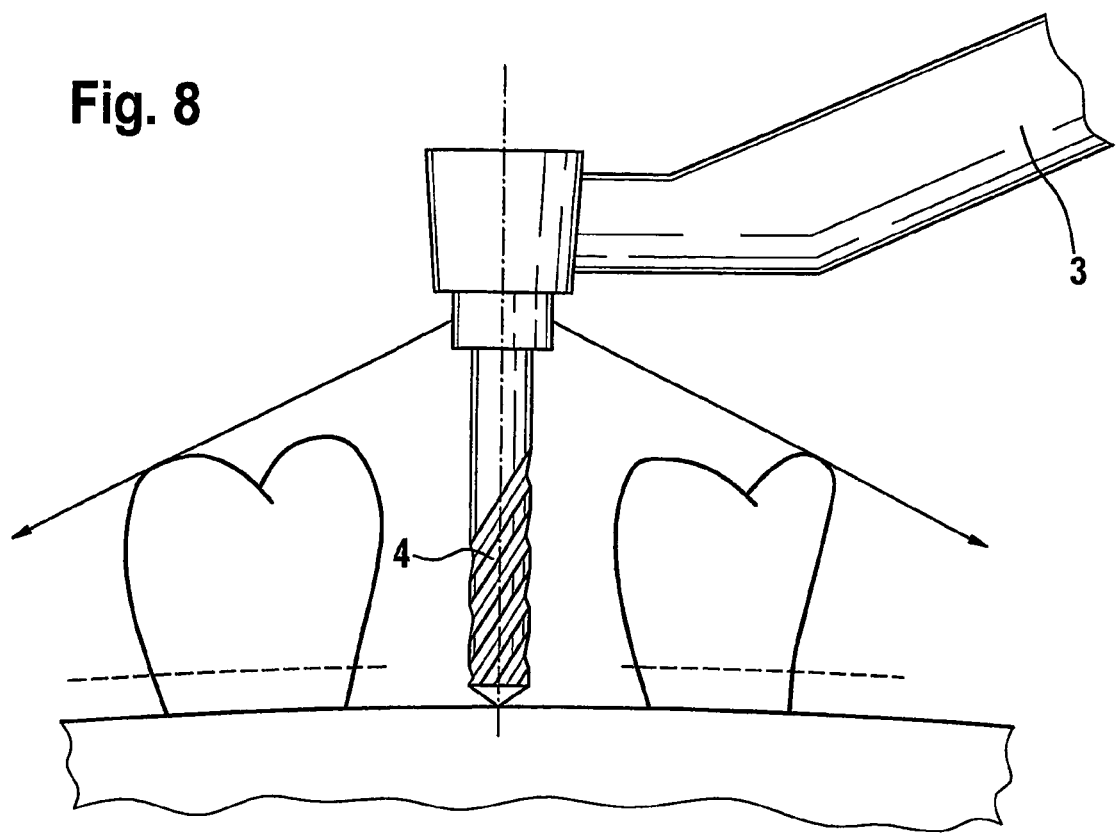
FIGS. 8-11 illustrate how the horizon line changes during machining up to an end position.
Figure 9:
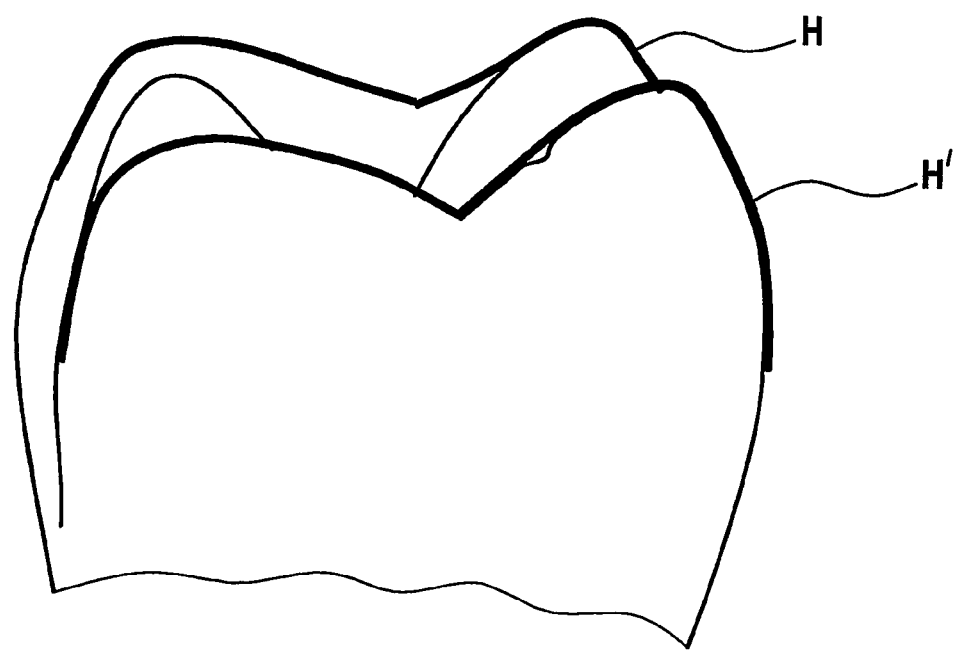
Figure 10:
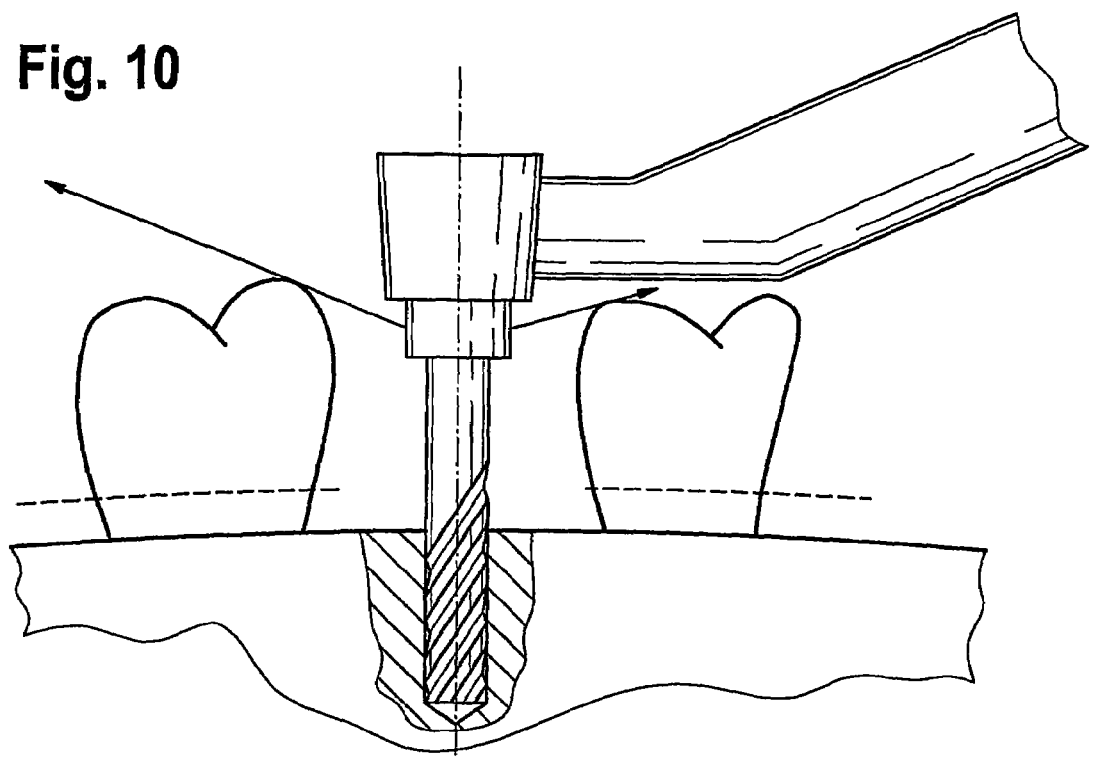
Figure 11:
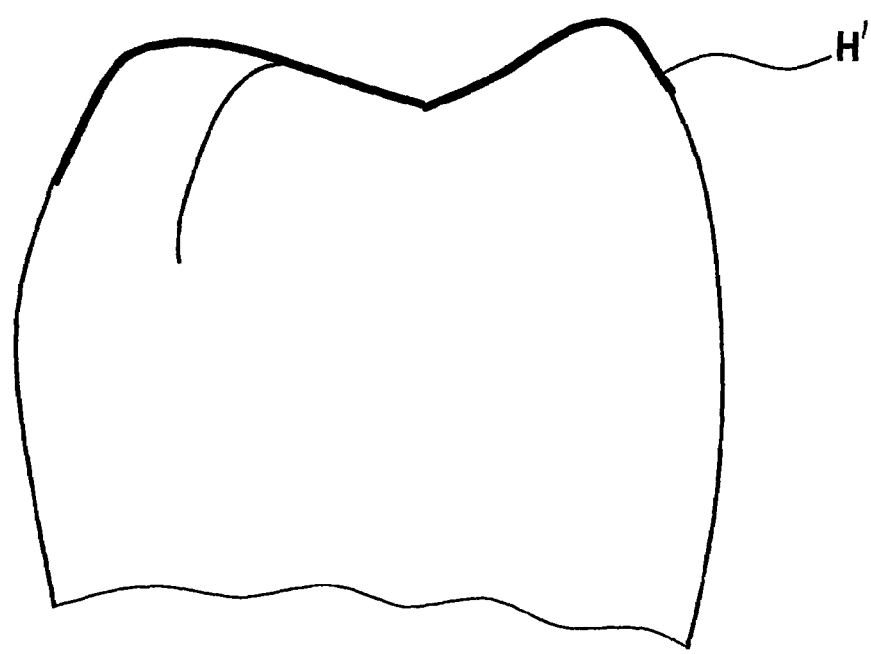

When the drill is in the correct position, as shown in FIG. 7, the operator begins to drill into the bone. The system now displays that horizon line to which the user may drill. FIG. 8 shows the properly positioned tool 4 of hand instrument 3. FIG. 9 shows the associated horizon line. The matching horizon line H in the background shows that the model point for drilling has been correctly found. A second, non-matching horizon line H' in the foreground becomes visible following commencement of drilling. When the drill reaches its computed end position according to FIG. 10, this horizon line H' will then match the displayed image of the tooth, see FIG. 11. The scene filmed by the camera changes during the drilling operation so that the horizon line H' will now be coincident with the visible horizon.

The method is carried out as follows: the surface of tooth or jaw is marked with X-ray-opaque markings, which enable correlation of 3D spatial measurement data obtained from X-ray images with 3D data obtained by scanning the surface. The X-ray-opaque markers are visible in the X-ray image as well as in the surface image. They make it possible to define the location of the two images relative to each other.

An implantation strategy is worked out with the aid of the X-ray images. This includes defining the drilling depth and the angle of the drilled channel.

The horizon line associated with all positions of the machining tool along the drilled channel is computed from the 3D surface-scanning data.

The instrument for creating the implantation hole has an intra-oral video camera positioned at a known distance from the tip of the drilling instrument. The computed horizon line for the target position is scanned into the video image produced by this camera, with all optical distortions accounted for. The superimposed horizon line can be brought into coincidence with the actually visible horizon by changing the position and angle of the drilling instrument.

During creation of the implantation hole, the horizon lines thus generated are viewed continuously to ensure that drilling continues in the correct direction.

Figure 12:
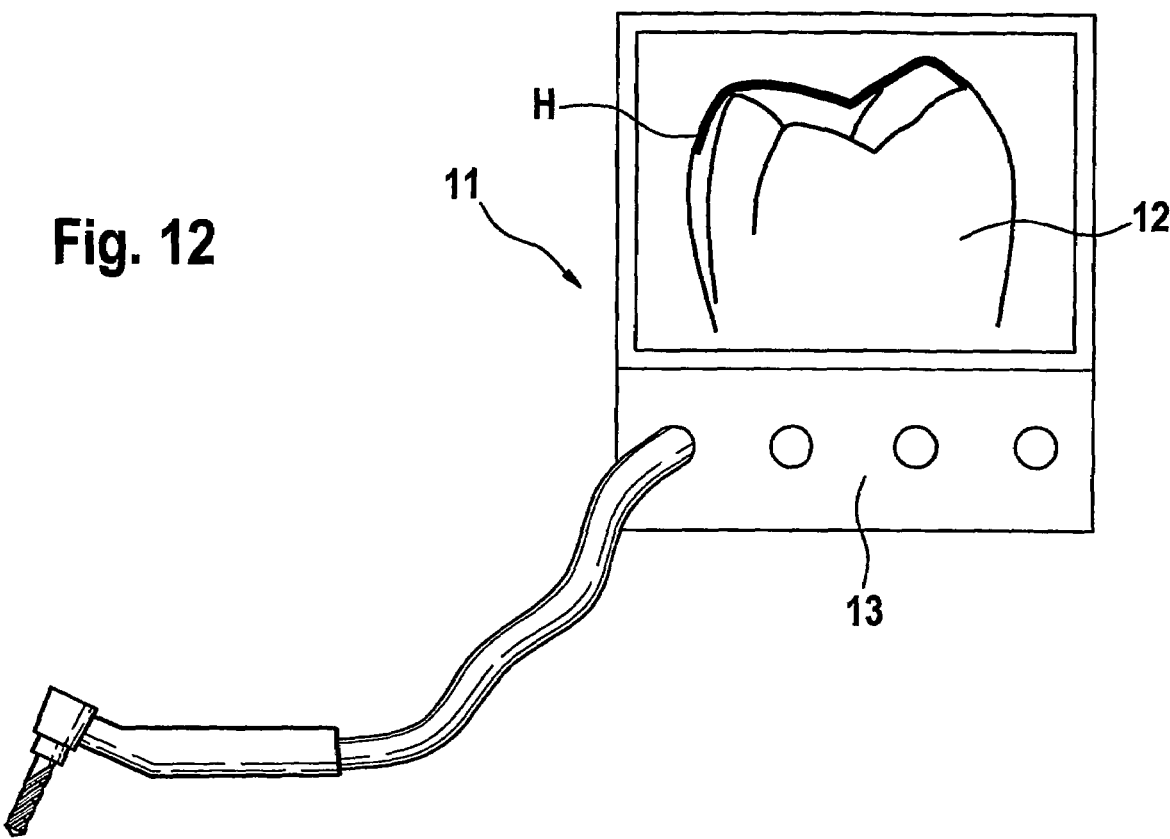
FIG. 12 shows diagrammatically a setup for carrying out the method.

A setup is illustrated diagrammatically in FIG. 12. Unit 11 comprises a display 12, on which images recorded by hand instrument 3 can be displayed. At the same time, an evaluating unit 13 controls the drill driver and computes the surface feature, in this case the horizon line. The instrument can be con-trolled such that the machining tool driver will be shut off when a deviation from the specified position is detected and released for a restart only when the correct position has been regained.

LIST OF REFERENCE NUMERALS OF CHARACTERS 1 tooth
2 tooth
3 hand instrument
4 tool
5 end of the hand instrument
6 attachment
7 tip of tool 4
8 drill-hole
9
10
11 unit
12 display
13 evaluating unit
A position/center of the viewer
B point
C horizon
E axis
H horizon line
H' horizon line
P projection screen
R radius
W

The invention claimed is:

1. A method of moving a hand instrument which includes a machining tool and a camera located at a specific distance from the machining tool to provide a cavity in a bone for a dental implant at a preparation site, comprising the following steps:

computing position-dependent surface features of a three-dimensional data set relating to a surface of an area at the preparation site relative to a desired position of the implant, the area in which the cavity is to be created being adjacent a tooth defining a horizon line and present in the form of a three-dimensional set of volume data;

detecting at least one section of the preparation site which exhibits a visible real surface feature by means of the camera on the hand instrument and a display providing a video image; and superimposing a computed surface feature for a target position of said hand instrument such that altering the position and angle of said hand instrument causes a change in the position of said superimposed surface feature relative to the visible real surface feature, and moving the hand instrument relative to the preparation site until the computed horizon line coincides with the horizon line of the adjacent tooth.

2. A method as defined in claim 1, wherein during a machining operation always those surface features which are computed for the current position of said hand instrument are superimposed over said video image, the current position of said hand instrument corresponding to a position of the implant within said cavity.

3. A method as defined in claim 1, wherein the machining tool includes a tip whose distance from the camera is known, wherein the hand instrument transmits an image produced in the camera to said display, and wherein the computed horizon line is computed in an evaluating unit to enable the hand instrument to be controlled when creating or excavating a cavity in a bone to an end position wherein the computed horizon lines of an adjacent tooth coincides with the visible camera-generated horizon line of the tooth.

* * * * *